US009988694B2

(12) United States Patent
Sung (10) Patent No.: US 9,988,694 B2
(45) Date of Patent: Jun. 5, 2018

(54) EFFECT OF HBV ON CLINICAL OUTCOME OF HEPATOCELLULAR CARCINOMA CANCER PATIENTS (71) Applicant: Agency for Science, Technology and Research, Singapore (SG)

(72) Inventor: Wing-Kin Sung, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days. days.

(21) Appl. No.: 14/439,967

(22) PCT Filed: Oct. 30, 2013

(86) PCT No.: PCT/SG2013/000469
§ 371 (c)(1),
(2) Date: Apr. 30, 2015

(87) PCT Pub. No.: WO2014/070114
PCT Pub. Date: May 8, 2014

(65) Prior Publication Data
US 2015/0275317 A1 Oct. 1, 2015

(30) Foreign Application Priority Data

Oct. 30, 2012 (SG) ................ 201208024-8

(51) Int. Cl.
C12Q 1/70 (2006.01)
C12Q 1/68 (2018.01)
(52) U.S. Cl.
CPC ........... *C12Q 1/706* (2013.01); *C12Q 1/6886* (2013.01); *C12Q 2600/118* (2013.01); *C12Q 2600/156* (2013.01); *C12Q 2600/158* (2013.01)

(58) Field of Classification Search
None
See application file for complete search history.

(56) References Cited

U.S. PATENT DOCUMENTS

| 7,439,020 | B2 * | 10/2008 | Sung | ...................... C12Q 1/706 435/6.12 |
| 2004/0072185 | A1 | 4/2004 | Paterlini-Brechot et al. | |
| 2006/0057601 | A1 | 3/2006 | Sung et al. | |
| 2006/0057670 | A1 | 3/2006 | Sung et al. | |
| 2008/0160510 | A1 | 7/2008 | Inoue et al. | |

FOREIGN PATENT DOCUMENTS

WO    WO-2014/070114    5/2014

OTHER PUBLICATIONS

Arguedas, Miguel R., et al., "Screening for Hepatocellular Carcinoma in Patients With Hepatitis C Cirrhosis: a Cost-Utility Analysis", *Am J Gastroenterol*, 98(3), (2003), 679-690.

Chan, H. L.-Y., et al., "Genotype C hepatitis B virus infection is associated with an increased risk of hepatocellular carcinoma", *Gut*, 53, (2004), 1494-1498.

Hao, Ke, et al., "Predicting prognosis in hepatocellular carcinoma after curative surgery with common clinicopathologic parameters", *BMC Cancer*, 9: 389, (2009), 11 pgs.

Hoshida, Yujin, et al., "Integrative transcriptome analysis reveals common molecular subclasses of human hepatocellular carcinoma", *Cancer Res*, 69(18), (2009), 7385-7392.

Kan, Zhengyan, et al., "Whole-genome sequencing identifies recurrent mutations in hepatocellular carcinoma", *Genome Res*, 23, (2013), 1422-1433.

Kao, J. H., et al., "Basal Core Promoter Mutations of Hepatitis B Virus Increase the Risk of Hepatocellular Carcinoma in Hepatitis B Carrier", *Gastroenterology*, 124, (2003), 327-334.

Lin, C. L., et al., "Clinicopathological differences between hepatitis B viral genotype B- and C-related resectable hepatocellular carcinoma", *Journal of Viral Hepatitus*, 14(1), (2007), 64-69.

Mahtab, Mamun-Al, et al., "Hepatitis B virus genotypes: an overview", *Hepatobiliary Pancreat Dis Int*, 7(5), (2008), 457-464.

Midorikawa, Yutaka, et al., "Microarray-based analysis for hepatocellular carcinoma: from gene expression profiling to new challenges", *World J Gastroenterol*, 13(10), (2007), 1487-1492.

Naito, Hideo, et al., "Rapid and Specific Genotyping System for Hepatitis B Virus Corresponding to Six Major Genotypes by PCR Using Type-Specific Primers", *J Clin Microbiol*, 39(1), (2001), 362-364.

Raimondi, Sara, et al., "Hepatitis C virus genotype 1b as a risk factor for hepatocellular carcinoma development: a meta-analysis", *Journal of Hepatology*, 50, (2009), 1142-1154.

Roffi, Luigi, et al., "Outcome of liver disease in a large cohort of histologically proven chronic hepatitis C: influence of HCV genotype", *Eur J Gastroenterol Hepatol*, 13, (2001), 501-506.

Sung, Joseph J. Y., et al., "Genotype-Specific Genomic Markers Associated with Primary Hepatomas, Based on Complete Genomic Sequencing of Hepatitis B Virus", *J Virol*, 82, (2008), 3604-3611.

Xu, Xun, et al., "The Genomic sequence of the Chinese Hamster ovary (CHO)-K1 cell line", *Nat Biotechnol*, 29(8), (2011), 735-741.

Yu, Mming-Whei, et al., "Hepatitis B virus Genotype and DNA Level and Hepatocellular Carcinoma: A Prospective Study in Men", *J. Natl. Cancer Inst.*, 97(4), (2005), 265-272.

"International Application No. PCT/SG2013/000469, International Search Report and Written Opinion dated Feb. 4, 2014", (Feb. 4, 2014), 10 pgs.

Sung, Wing-Kin, et al., "Genome-wide survey of recurrent HBV integration in hepatocellular carcinoma", Nature Genetics, vol. 44. No. 7, Jul. 2012, 765-769, (Jul. 2012), 765-769.

"European Application Serial No. 13851719.8, European Search Report dated May 3, 2016", (May 3, 2016) 9 pgs.

* cited by examiner

*Primary Examiner* — Stacy B Chen
(74) *Attorney, Agent, or Firm* — Schwegman Lundberg & Woessner, P.A.

(57) ABSTRACT

A method for predicting prognosis (clinical outcome) of hepatocellular carcinoma patients based on the detection of a Hepatitis B virus, determination of the HBV genotype, identification of the strain of the HBV genotype and its integration into the genome, in biological samples of such patients is provided.

3 Claims, 2 Drawing Sheets

EFFECT OF HBV ON CLINICAL OUTCOME OF HEPATOCELLULAR CARCINOMA CANCER PATIENTS

This application is a U.S. national stage application filed under 35 U.S.C. § 371 from International Application Serial No. PCT/SG2013/000469, which was filed 30 Oct. 2013, and published as WO 2014/070114 on 8 May 2014, and which claims the benefit of priority of Singapore Patent Application No. 201208024-8, filed 30 Oct. 2012, the contents of it being hereby incorporated by reference in its entirety for all purposes which applications and publication are incorporated by reference as if reproduced herein and made a part hereof in their entirety, and the benefit of priority of each of which is claimed herein.

FIELD OF THE INVENTION

The present invention relates to a method of determining a clinical outcome of hepatocellular carcinoma (HCC) patients using the presence, genotype and strain of a Hepatitis B virus (HBV) in a sample from the patient. In particular, the invention relates to the prognosis of HCC patients.

BACKGROUND

Hepatocellular carcinoma (HCC) is the 5th most common solid cancer world-wide and the 3rd and 6th most frequent cause of cancer death in men and women, respectively. HCC patients have high death rate and high recurrence rate. The ability to determine HCC survival and HCC recurrence earlier is important.

Currently, the most common diagnosis method for HCC is based on measuring the serum alpha-fetoprotein (AFP) levels in conjunction with hepatic ultrasonography. Ultrasonography screening was found to be cost-effective but has only 60% sensitivity and 97% specificity in cirrhotic patients[1]. Serum AFP is only elevated in 40-60% of HCC patients largely at a very advanced stage or do not produce AFP at all.

Since many HCC cases are expected to be induced by HBV and Hepatitis C virus (HCV), the HBV and HCV in the patient samples may be a good indicator of clinical outcome. For HCV, previous reports showed that the genotype increases the risk of developing HCC[2,3]. For HBV, some previous reports showed that HBV genotypes are likely to be important in determining the severity and progression of HBV-induced liver disease[4]. However, no conclusive result is known. It is known that genotype C HBV is associated with a higher risk of HCC than genotype B HBV, which is probably related to a delayed HBeAg seroconversion, more active hepatitis, and a higher prevalence of basal core promoter mutations [5,6,7] The precore (G1896A) and core promoter (A1762T, G1764A) mutations of the HBV gene are known to be associated with changes in immunologic phase or the progression to complicated liver disease in adults. HBV with TCC at nucleotides 1856 to 1858 of the precore region might represent a specific HBV strain associated with more aggressive liver disease than other genotype C HBV strains[8]. Sung et al. demonstrated that HBV genotype Ce is associated with a higher risk of HCC and cirrhosis when compared to genotypes B and Cs[9]. However, the result is not statistically significant.

With the development of health awareness in the general public, HCC comes to medical attention at earlier stages where often it is hard to determine the prognosis using classical histopathological measurements such as tumor multinodularity and vascular invasion.

Furthermore, all previous reports only disclose the relationship between genotypes and the risk of HCC and/or cirrhosis. Currently there is no reliable guide on the relationship between HBV genotypes and other clinical parameters like survival and recurrence.

SUMMARY OF THE INVENTION

The present disclosure provides a method for making a prognosis with respect to the clinical outcome of hepatocellular carcinoma (HCC) in a patient comprising the steps of a) detecting the presence of a Hepatitis B virus (HBV) in a sample obtained from said patient; b) identifying the genotype of said HBV in said sample; and c) making a prognosis with respect to the clinical outcome of HCC based on the identity of the HBV genotype detected.

DEFINITIONS

This section is intended to provide guidance on the interpretation of the words and phrases set forth below (and where appropriate grammatical variants thereof). Further guidance on the interpretation of certain words and phrases as used herein (and where appropriate grammatical variants thereof) may additionally be found in other sections of this specification.

The invention illustratively described herein may suitably be practiced in the absence of any element or elements, limitation or limitations, not specifically disclosed herein. Thus, for example, the terms "comprising", "including", "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of" A and SET (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

The term "HCC" as used herein includes all forms of HCC including stage I, II, III (subclasses IIIA, IIIB and IIIC) and IV (subclasses IVA and IVB) HCC Optionally, the HCC may be: (a) stage I; (b) stage II; (c) stage I or II; (d) stage II or III; (e) stage I, II or III; (f) stage II, III or IV; or (g) stage I, II, III or IV.

The term "patient" as used herein includes human patients and other mammals and includes any individual that is, or has been, afflicted with HCC, or which it is desired to analyse or treat using the methods of the invention. Suitable mammals that fall within the scope of the invention include, but are not restricted to, primates, livestock animals (eg. sheep, cows, horses, donkeys, pigs), laboratory test animals (eg. rabbits, mice, rats, guinea pigs, hamsters), companion animals (eg. cats, dogs) and captive wild animals (eg. foxes, deer, dingoes). Preferably, the patient is a human patient. The patient may be male or female. Optionally, the patient may be undergoing treatment, for example experimental treatment, for HCC. The patient may have stage I, II, III (subclasses IIIA, IIIB and IIIC) and IV (subclasses IVA and IVB) HCC. Optionally, the patient is: (a) a stage I or II patient; (b) a stage II or III patient.

The term "prognosis" as used herein includes a reference to predicting the likelihood of HCC-attributable death or progression, including recurrence, Edmondson grade, venous infiltration, tumor size, overall survival, and disease free survival venous infiltration, cirrhosis and other histological abnormalities.

As used herein, the term "nucleic acid" designates a molecule comprising one or more nucleotides, or an oligonucleotide, or a fragment thereof, including but not limited to RNA or DNA nucleotides or combinations thereof.

As used herein, the term "isolated" means that a nucleotide sequence, for example a gene, primer, or oligonucleotide or other sequence is substantially or essentially free from other nucleic acids or other impurities.

As used herein, the term "amplicon", "amplified product" or "amplification product" refers to a product of an amplification reaction. An example of an amplicon is a nucleotide sequence produced as a result of PCR, real-time PCR, reverse transcription-PCR, competitive RT-PCR, ligase chain reaction (LCR), gap. LCR, strand displacement amplification (SDA), nucleic acid sequence based amplification (NASBA), transcription-mediated amplification (TMA), rolling circle amplification (RCA) or the like.

The term "primer" is used herein to mean any single-stranded oligonucleotide sequence capable of being used as a primer in, for example, PCR or RCA technology. Thus, a "primer" according to the disclosure refers to a single-stranded oligonucleotide sequence that is capable of acting as a point of initiation for synthesis of a primer extension product that is substantially identical to the nucleic acid strand to be copied (for a forward primer) or substantially the reverse complement of the nucleic acid strand to be copied (for a reverse primer). A primer may be suitable for use in, for example, PCR technology. Single-stranded includes, for example, hairpin structures formed by single-stranded nucleotide sequences. The design of a primer, for example its length and specific sequence, depends on the nature of the target nucleotide sequence and on the conditions at which the primer is used, for example, temperature and ionic strength.

The primers may consist of the nucleotide sequences described herein, or may be 10, 15, 20, 25, 30, 35, 40, 45, 50, 75, 100 or more nucleotides which comprise or fall within the sequences described herein, provided they are suitable for specifically binding a target nucleic acid sequence, under stringent conditions. In one embodiment, the primer sequence is less than 35 nucleotides in length, for example the primer sequence is less than 34, 33, 32, 31, 30, 29, 28, 27, 26, 25, 24, 23, 22 21 20 19 18 17 16 15 14 13 12 11 or 10 nucleotides in length. Slight modifications of the primers or probes, in length or in sequence, can be carried out to maintain the specificity and sensitivity required under the given circumstances. In one embodiment of the present disclosure, probes and/or primers described herein may be extended in length by 1, 2, 3, 4 or 5 nucleotides or reduced in length by 1, 2, 3, 4 or 5 nucleotides, for example, in either direction. Primer sequences can be synthesised using any methods well known in the art.

As used herein, the terms "amplification" refers to an amplification reaction, for example an enzyme-mediated reaction used to amplify a specific target nucleotide sequence. By amplifying the target nucleotide sequence, the reaction produces many more copies of the target nucleotide sequence to produce an amplicon, amplified product or amplification product. One example of an amplification reaction is a "polymerase chain reaction' (PCR)". PCR is carried out with the aid of thermal cycler in a mixture containing a polymerase enzyme, a set of primers, for example a set of forward and reverse primers and any additional primers that may be required and four deoxynucleotide triphosphates- (dNTPs).

The terms "biological material" or "biological sample" as used herein refers to any material or sample, which includes an analyte as defined herein. Such samples may, for example, include samples derived from or comprising stool, whole blood, serum, plasma, tears, saliva, nasal fluid, sputum, ear fluid, genital fluid, breast fluid, milk, colostrum, placental fluid, amniotic fluid, perspirate, synovial fluid, ascites fluid, cerebrospinal fluid, bile, gastric fluid, aqueous humor, vitreous humor, gastrointestinal fluid, exudate, transudate, pleural fluid, pericardial fluid, semen, upper airway fluid, peritoneal fluid, fluid harvested from a site of an immune response, fluid harvested from a pooled collection site, bronchial lavage, urine, biopsy material, e.g. from all suitable organs, e.g. the lung, the muscle, brain, liver, skin, pancreas, stomach, etc., a nucleated cell sample, a fluid associated with a mucosal surface, hair, or skin.

The terms "treatment", "therapeutic intervention" and "therapy" may be used interchangeably herein (unless the context indicates otherwise) and these terms refer to both therapeutic treatment and prophylactic or preventative measures, wherein the aim is to try and prevent or slow down (lessen) the targeted pathologic condition or disorder. In tumor treatment, the treatment may directly decrease the pathology of tumor cells, or render the tumor cells more susceptible to treatment by other therapeutic agents, e.g., radiation and/or chemotherapy. The aim or result of tumor treatment may include, for example, one or more of the following: (1) inhibition (i.e., reduction, slowing down or complete stopping) of tumor growth; (2) reduction or elimination of symptoms or tumor cells; (3) reduction in tumor size; (4) inhibition of tumor cell infiltration into adjacent peripheral organs and/or tissues; (5) inhibition of metastasis; (6) enhancement of anti-tumor immune response, which may, but does not have to, result in tumor regression or rejection; (7) increased survival time; and (8) decreased mortality at a given point of time following treatment. Treatment may entail treatment with a single agent or with a combination (more than two) of agents. An "agent" is used herein broadly to refer to, for example, a drug/compound or other means for treatment e.g. radiation treatment or surgery. Examples of treatment include surgical intervention, liver transplantation, immunotherapy, chemotherapy with a given drug or drug combination, radiation therapy, neoadjuvant treatment, diet, vitamin therapy, hormone therapies, gene therapy, cell therapy, antibody therapy etc. The term "treatment" also includes experimental treatment e.g. during drug screening or clinical trials.

Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

DISCLOSURE OF OPTIONAL EMBODIMENTS

Exemplary, non-limiting embodiments of a method for making a prognosis with respect to the clinical outcome of hepatocellular carcinoma (HCC) in a patient will now be described. In one embodiment the method may comprise the steps of: (a) detecting the presence of a Hepatitis B virus (HBV) in a sample obtained from said patient; (b) identifying the genotype of said HBV in said sample; and (c) making a prognosis with respect to the clinical outcome of HCC based on the identity of the HBV genotype detected.

In one embodiment, the said step of detecting the presence of said genotype of HBV may further comprise detecting if said HBV genotype has integrated into the genome of said patient.

In one embodiment, the said step of determining whether said HBV genotype has integrated into said genome may further comprise identifying if said HBV genotype has integrated into one or more genes in said genome. In one embodiment, the one or more genes may be selected from the group consisting of hTERT, MLL4, CCNE1, SENP5 and ROCK1. In one embodiment, the one or more genes may be hTERT, MLL4 or CCNE1.

In one embodiment, the sample may comprise a nucleic acid obtained from a biological material.

In one embodiment, the nucleic acid may be selected from a single or double-stranded RNA or DNA molecule, cDNA and genomic DNA. In one embodiment, the nucleic acid may be genomic DNA.

In one embodiment, the biological material may be selected from the group consisting of a sample of fresh tissue, frozen tissue, paraffin-preserved tissue and/or ethanol preserved tissue. In another embodiment, the biological material may be selected from the group consisting of whole blood or a component thereof, lymph, bile fluid, cerebrospinal fluid, bronchioalveolar lavage fluid, synovial fluid, semen, ascitic tumour fluid, breast milk, amniotic fluid, a buccal smear and pus.

In one embodiment, the genotype of HBV may be selected from the group consisting of HBV genotype A, HBV genotype B, HBV genotype C, HBV genotype D, HBV genotype E, HBV genotype F, HBV genotype G and HBV genotype H.

In one embodiment, the HBV genotype A may be selected from the group consisting of subtype A1, A2 and A3.

In one embodiment, the HBV genotype B may be selected from the group consisting of subtype B1, B2, B3 and B4. In one embodiment, the HBV genotype B may be HBV-B2.

In one embodiment, the HBV genotype D may be selected from the group consisting of subtype D1, D2, D3 and D4.

In one embodiment, the HBV genotype F may be selected from the group consisting of subtype F1 and F2.

TABLE 3

Taqman primers and probes for detecting different strains.

| HBV Strain | ForwardPrimer | qPCR | ReversePrimer | Forward Primer Pos | qPCR Pos | Reverse Primer Pos | Product Len |
|---|---|---|---|---|---|---|---|
| 1182 | Ctacagcatgggaggttggt (SEQ ID NO:1) | Ctccaccccacggcagtctt (SEQ ID NO:2) | Gctgctggcactgttgtcaa (SEQ ID NO:3) | 2841 | 3050 | 3119 | 279 |
| HK858 | Tcccutttaccgctgttacc (SEQ ID NO:4) | Tactaaaactaaacgttggg (SEQ ID NO:5) | Ccccacaattcgttgacata (SEQ ID NO:6) | 784 | 840 | 1005 | 222 |
| HK858 | Ttggggaggagactaggtt (SEQ ID NO:7) | Gttcatgtctcactgttcaa (SEQ ID NO:8) | Tcaatgtccatgccccaaag (SEQ ID NO:9) | 1740 | 1848 | 1912 | 173 |
| HK2100 | Gattcactttctctcgccaac (SEQ ID NO:10) | Aaaactcatcggaaccgaca (SEQ ID NO:11) | Ctagcagccatggaaaggag (SEQ ID NO:12) | 1087 | 1317 | 1384 | 298 |
| GZ-DYH | Ctgggaggctgtaggcataa (SEQ ID NO:13) | Cttttcactcctgcctaat (SEQ ID NO:14) | Atacagagcagaggcggtgt (SEQ ID NO:15) | 1773 | 1820 | 2014 | 242 |
| CHN- | Tattgggggccaagtctgta | Tcccttaaccttatgggata | Gtgtaaaaggggcagcaaag | 752 | 865 | 1033 | 282 |

TABLE 3-continued

Taqman primers and probes for detecting different strains.

| HBV Strain | ForwardPrimer | qPCR | ReversePrimer | Forward Primer Pos | qPCR Pos | Reverse Primer Pos | Product Len |
|---|---|---|---|---|---|---|---|
| H172 | (SEQ ID NO:16) | (SEQ ID NO:17) | (SEQ ID NO:18) | | | | |
| CHN-H155 | Ggcaaactccctctmcct (SEQ ID NO:19) | Cctgaacacatagttaatca (SEQ ID NO:20) | Aggcgctgcgagtagntct (SEQ ID NO:21) | 2527 | 2706 | 2805 | 279 |
| HBV-B2 | Ttgggggccaagtctgta (SEQ ID NO:22) | Atattgtaagaaaaatcaaa (SEQ ID NO:23) | Tatccacattgcgtgaaagg (SEQ ID NO:24) | 754 | 920 | 1043 | 290 |
| HBV-B2 | Catgaaccttttaccccgttg (SEQ ID NO:25) | Caagtgtttcgtgacgcaac (SEQ ID NO:26) | Gacgggacgtaaacaaagga (SEQ ID NO:27) | 1134 | 1177 | 1436 | 303 |
| CHN-H155 C2288 | Actgttcttgagtatttggtg (SEQ ID NO:28) | Tcgcactcctcccgcttacag (SEQ ID NO:29) | Tgacatctattgataatatcctctttc (SEQ ID NO:30) | 2240 | 2288 | 2558 | 319 |
| CHN-H155 A2288 | Actgttcttgagtatttggtg (SEQ ID NO:31) | Tcgcactcctaccgcttacag (SEQ ID NO:32) | Tgacatctattgataatatcctctttc (SEQ ID NO:33) | 2240 | 2288 | 2558 | 319 |

In one embodiment, the HBV genotype C may be selected from the group consisting of subtype C1, C2, C3, C4 and C5. In another embodiment, the HBV genotype C may be selected from the group consisting of CHN-H155, GZ-DYH, CHN-H172, HK2100, HK858 and I182 and variants, including biologically active variants, thereof. In yet another embodiment, the HBV genotype C may be CHN-H155. In one embodiment, the CHN-H155 may comprise the mutation C2288A.

In one embodiment, the nucleic acid sample may be amplified by a polymerase chain reaction into one or more amplicons. In one embodiment, the one or more amplicons may be subjected to sequencing. In one embodiment, the sequence of the one or more amplicons may be compared with sequences of known HBV genotypes to determine the HBV genotype in the sample.

In one embodiment, the HBV strain may be selected from CHN-H155, GZ-DYH, CHN-H172, HK2100, HK858, I182 and HBV-B2.

In one embodiment, the step of making a prognosis with respect to the clinical outcome may comprise correlating the genotype of said HBV in said patient sample with one or more factors associated with said HBV genotype in said patient relative to a patient having another HBV genotype.

In one embodiment, the one or more factors may be selected from one or more of HBV genomic integration, genomic data of said patient, mutational status of the HBV strain identified in said sample or transcriptome profile.

BRIEF DESCRIPTION OF THE FIGURES

The invention will be better understood with reference to the detailed description when considered in conjunction with the non-limiting examples and the accompanying drawings. The accompanying drawings illustrate a disclosed embodiment and serves to explain the principles of the disclosed embodiment. It is to be understood, however, that the drawings are designed for purposes of illustration only, and not as a definition of the limits of the invention.

FIG. 1 is a phylogenetic tree for the 7 HBV strains identified in the 84 out of 88 HCC patients. The 88 patients were diagnosed with HCC and underwent curative primary hepatectomy or liver transplantation at Queen Mary Hospital (Hong Kong, China).

FIG. 2(a) depicts the overall survival curve for the 20 HCC patients carrying HBV GZ-DYH, compared with HCC patients with other HBV genotypes. FIGS. 2(b) and (c) depict the overall survival and disease survival curves for the 31 HCC patients carrying HBV CHN-H155, compared with HCC patients with other HBV genotypes. FIG. 2(d) depicts the disease free survival curve for the 6 HCC patients carrying HBV CHN-H172, compared with HCC patients with other HBV genotypes.

BRIEF DESCRIPTION OF THE TABLES

Table 1. Summary of the relationship between HBV strains, genotypes and the clinical data. The clinical data includes venous infiltration, recurrence, overall and disease free survival, Edmondson grade and histology of 88 Chinese patients diagnosed with HCC who underwent curative primary hepatectomy or liver transplantation at Queen Mary Hospital (Hong Kong, China).

Table 2. Summary of the relationship between HBV strains, genotypes and the genomic variations. The expression subclasses, S1, S2 and S3, are based on the defined gene signatures of Hoshida et al. p53 SNP and CTNNB1 SNP represents single nucleotide polymorphisms at the p53 and CTNNB1 genes.

Table 3. Number of HBV integrations for HCC patients with different HBV strains.

Table 4. Locations of HBV integrations for HCC patients with different HBV strains. The locations are either in the exon, intron or promoter region of genes.

Table 5. Potential treatment and prevention schemes for HCC patients carrying different HBV strains.

EXPERIMENTAL SECTION

Non-limiting examples of the invention, including the best mode, and a comparative example will be further described in greater detail by reference to specific Examples, which should not be construed as in any way limiting the scope of the invention.

Example 1

Effect of HBV on clinical outcome of HCC cancer patients

Materials and Methods
Patient Samples and Data Preparation

A total of 88 Chinese patients diagnosed with HCC who underwent curative primary hepatectomy or liver transplantation at Queen. Mary Hospital (Hong Kong, China) were included in this study. All patients gave written informed consents to use both tumor (T) and non-tumor (N) liver tissues for the study as previously described by Hao et al.[10]

Genomic DNA were purified for at least 30-fold coverage paired-end (PE) sequencing according to the previously reported method by Xu et al.

Two sequencing libraries with different insert sizes were constructed for each genomic DNA sample. DNA was fragmented by an ultrasonicator Covaris E-210 (Covaris, Woburn, Mass.). By adjusting to related optimal shearing parameters, DNA fragments were set to be concentrated in 170 bp and 800 bp peaks for their related libraries. These fragments were purified, end blunted, "A" tailed, and adaptor ligated. 10 to 12 cycles of PCR were performed after size selection in the gel. The concentration of the libraries was quantified by bioanalyzer (Agilent Technologies, Santa Clara, Calif.) and qPCR method using ABI StepOne Plus real-time PCR system (Life Technologies, Carlsbad, Calif.). To obtain an optimal cluster number in the flowcell and accurate signal capture, 170 bp and 800 bp libraries were loaded to the flowcell in a 2:3 ratio. Paired-end, 90 bp read-length sequencing was performed with, the HiSeq 2000 sequencer according to Manufacturer's instructions (Illumina, San Diego, Calif.).

Determining the HBV Strain in Each Sample

For each sample, paired-end reads which could not be mapped to hg19 were retrieved. Those paired-end reads were mapped to 1901 HBV complete genomes using BLAST. The best hit of each read was assigned to the respective HBV genomes. Based on the number of hits and coverage, the best HBV strain was assigned to the sample.

Statistical Analysis

Statistical analysis was performed to determine whether each HBV strain affects the genomic data and clinical data, in particular, Edmondson grade, venous infiltration, recurrence, tumor size, overall survival, and disease free survival. For category data, Fisher exact test was performed to test if there is any relationship between the data and the HBV strain. For survival and disease-free survival, Kaplan-Meier analysis was performed.

Results

Generating the HBV Strains from the 88 Patients

Figure 1:
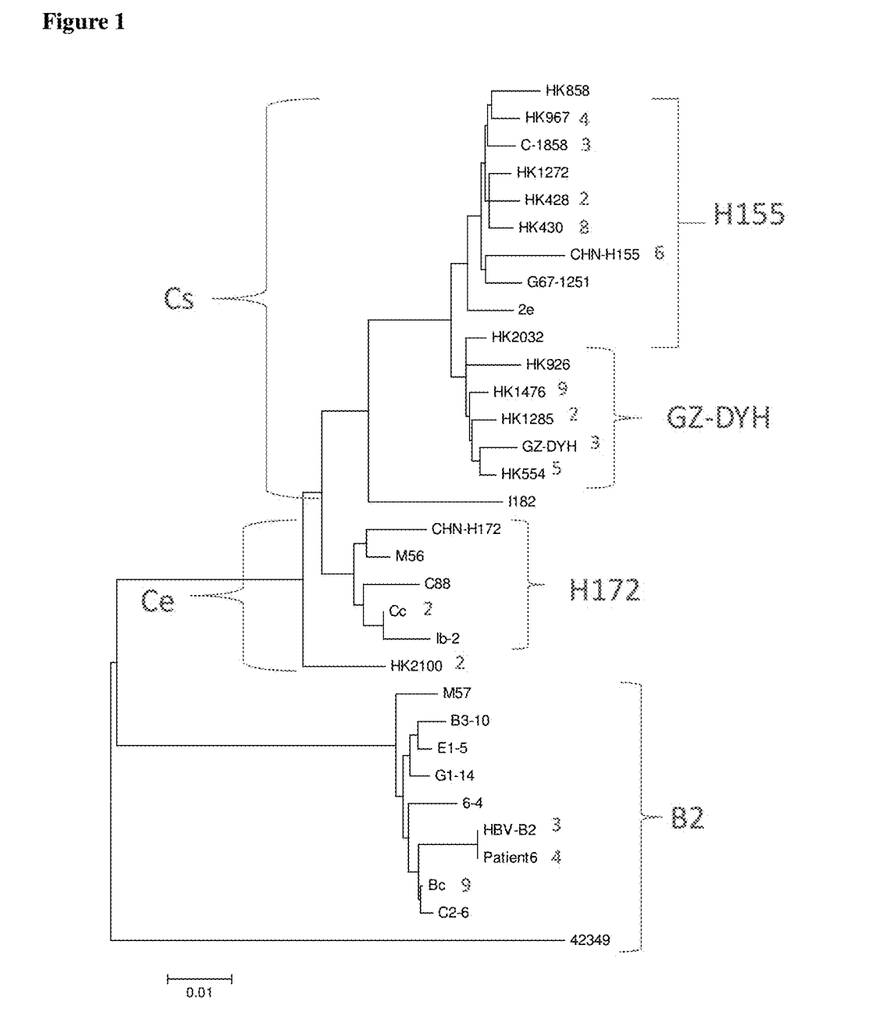

Among the eighty-eight patients, HBV strains were discovered for 84 of them. For eighty-one out of the 84 patients, the HBV strains predicted in both tumor and the adjacent non-tumor were the same. The 4 samples with no predicted HBV strains are all HbsAg negative samples. Both evidences indicate the method can accurately identify the correct HBV strains from the samples. Among the 84 samples, 7 distinct HBV strains were identified: CHN-H155, HBV-B2, GZ-DYH, CHN-H172, HK2100, HK858, and I182. These HBV strains are carried by 31, 23, 20, 6, 2, 1, and 1 HCC patients, respectively. Table 1 summarizes the details of the 7 HBV strains that were identified in the patients. FIG. 1 shows the phylogenetic tree for the 7 HBV strains. Apart from the 23 samples containing HBV-B2 which were genotype B, all remaining samples were of genotype C.

TABLE 1

Summary of the relationship between HBV strains, genotypes and the clinical data.

| HBV strains | | CHN-H155 | CHN-H172 | GZ-DYH | HBV-B2 | HK2100 | HK858 | I182 | Nil |
|---|---|---|---|---|---|---|---|---|---|
| Number of samples | | 31 | 6 | 20 | 23 | 2 | 1 | 1 | 4 |
| Genotype | | Cs | Ce | Cs | Ba | C | C | C | — |
| Venous Infiltration | Presence/Absent | 12/19 | 6/0 | 8/12 | 13/10 | 0/2 | 1/0 | 1/0 | 3/0 |
| | p-value | 0.07714 | 0.01303 | 0.2054 | 0.3369 | — | — | — | — |
| | | (absent) | | (absent) | | | | | |
| Recurrence | Yes/No | 12/19 | 6/0 | 14/6 | 15/8 | 1/1 | 1/0 | 0/1 | 2/2 |
| | p-value | 0.006756 (No) | 0.03323 | 0.1628 | 0.2843 | — | — | — | — |
| Overall survival p-value | | 0.0569 (alive) | 0.1 (dead) | 0.0605 (dead) | 0.514 | — | — | — | — |
| Disease Free survival p-value | | 0.0332 (alive) | 0.0315 (dead) | 0.101 (dead) | 0.327 | — | — | — | — |
| Edmondson grade | Poorly differentiated | 4 | 2 | 3 | 9 (p-value = 0.02964) | 0 | 1 | 0 | 0 |
| | Moderately differentiated | 14 | 3 | 13 | 10 | 1 | 0 | 1 | 3 |
| | Well differentiated | 5 | 0 | 3 | 2 | 1 | 0 | 0 | 1 |
| | NA | 8 | 1 | 1 | 2 | 0 | 0 | 0 | 0 |
| Histology | Chronic hepatitis | 7 | 1 | 3 | 8 | 1 | 0 | 0 | 2 |
| | Cirrhotic | 17 | 5 | 17 (p-value = 0.01959) | 14 | 0 | 1 | 0 | 1 |
| | Non-cirrhotic | 2 | 0 | 0 | 1 | 1 | 0 | 1 | 1 |
| | NA | 5 | 0 | 0 | 0 | 0 | 0 | 0 | 0 |

TABLE 2

Summary of the relationship between HBV strains, genotypes and the genomic variations.

| HBV strains | | CHN-H155 | CHN-H172 | GZ-DYH | HBV-B2 | HK2100 | HK858 | I182 | Nil |
|---|---|---|---|---|---|---|---|---|---|
| Number of samples | | 31 | 6 | 20 | 23 | 2 | 1 | 1 | 4 |
| Genotype | | Cs | Ce | Cs | Ba | C | C | C | — |
| Expression subclass | S1 | 10 | 2 | 7 | 7 | 0 | 0 | 0 | 0 |
| | S2 | 4 (not S2 p-value = 0.0304) | 2 | 3 | 9 (p-value = 0.03473) | 0 | 1 | 0 | 1 |
| | S3 | 16 | 2 | 10 | 7 (not S3 p-value = 0.0163) | 2 | 0 | 1 | 3 |
| p53 SNP | Yes/No | 8/23 | 2/4 | 6/14 | 10/13 | 1/1 | 0/1 | 0/1 | 1/3 |
| | p-value | 0.2587 (No) | 0.6254 | 0.6757 | 0.1285 | — | — | — | — |
| CTNNB1 SNP | Yes/No | 6/25 | 1/5 | 1/19 | 3/20 | 1/1 | 0/1 | 0/1 | 2/2 |
| | p-value | 0.358 | 0.6582 | 0.1167 (No) | 0.4731 (No) | — | — | — | — |

TABLE 2-continued

Summary of the relationship between HBV strains, genotypes and the genomic variations.

| HBV strains | | CHN-H155 | CHN-H172 | GZ-DYH | HBV-B2 | HK2100 | HK858 | I182 | Nil |
|---|---|---|---|---|---|---|---|---|---|
| HBV-TERT integration | Yes/No | 13/18 | 0/6 | 4/16 | 1/22 | 0/2 | 0/1 | 0/1 | 0/4 |
| | p-value | 0.0004042 | 0.2419 (No) | 0.6139 (No) | 0.01982 (No) | — | — | — | — |
| HBV-MLL4 integration | Yes/No | 1/30 | 0/6 | 3/17 | 5/18 | 0/2 | 0/1 | 0/1 | 0/4 |
| | p-value | 0.1054 | 0.5129 | 0.3326 | 0.04854 | — | — | — | — |
| HBV-CCNE1 integration | Yes/No | 2/29 | 0/6 | 2/18 | 0/23 | 0/2 | 0/1 | 0/1 | 0/4 |
| | p-value | 0.4416 | 0.7501 (No) | 0.2209 | 0.2903 (No) | — | — | — | — |

Correlation with HBV Integration

For the same 88 samples, Sung et al. discovered 399 HBV integrations in those genomes. One question is whether different HBV strains have different HBV integration patterns. It was first tested whether the HBV strains affect the HBV integration frequencies. With reference to Table 3, patients carrying CHN-H155 tend to have more HBV integrations (p-value=0.000223). CHN-H155 was found to preferentially integrate into the promoter (p-value=0.013) and intron (p-value=0.087) regions (Table 4). Patients carrying HBV-B2 tend to have less HBV integrations (p-value=0.006397, Table 3). Lastly, for patients carrying CHN-H172, the HBV tends to integrate into the intronic region (p-value=0.063, Table 4).

Next, it was studied whether different HBV strains have differential preferred integration regions. From Sung et al., there are 3 recurrent HBV integrations. They are HBV-TERT, HBV-MLL4 and HBV-CCNE1.

Table 2 shows the distribution of these HBV integrations depending on the HBV strains. CHN-H155 strain was found to preferentially integrate near the TERT gene. Out of 18 patients with HBV-TERT integrations, 13 of them carry CHN-H155 (p-value=0.000404). For patients carrying HBV-B2, the HBV preferred to integrate near the MLL4 gene. Out of 9 patients with HBV-MLL4 integrations, 5 of them carry HBV-B2 (p-value=0.04854).

TABLE 3

Number of HBV integrations for HCC patients with different HBV strains.

| HBV strain | Number of integrations | Fraction | Binomial p-value |
|---|---|---|---|
| CHN-H155 | 181 | 0.453634 | 0.000223 |
| GZ-DYH | 94 | 0.235589 | 0.480655069 (less than expected) |
| HBV-B2 | 87 | 0.218045 | 0.0006397 (less than expected) |
| CHN-H172 | 34 | 0.085213 | 0.123349 |
| Others | 3 | 0.007519 | 0.00000538 (less than expected) |

Correlation with the Genomic Data of the Patients

The relationship between HBV strain and point mutations was investigated. The two key mutated genes in HCC are p53 and CTNNB1. Patients with HBV-B2 were more likely to have p53 mutation (odd ratio=2.008, p-value=0.1285, Table 2). For patients with GZ-DYH, they were less likely to have CTNNB1 mutation (odd ratio=4.49, p-value=0.1167).

Next, it was investigated whether HBV strain is associated with the transcriptome. The gene expression profiles of the 88 samples had previously been determined 12 using Hoshida et al.'s defined gene signatures 13 (subclassified into 3 classes S1, S2, and S3). Table 2 shows the distribution of S1, S2 and S3 with respect to the different HBV strains. It was observed that patients with CHN-H155 and GZ-DYH were unlikely to be of gene signature subclass S2 (p-values=0.0304 and 0.0977, respective). On the other hand, patients with HBV-B2 were likely to be of gene signature subclass S2 (p-value=0.03473) but unlikely to be of subclass S3 (p-value=0.0163). These data showed that the HBV strains affect the transcriptome profile of HCC patients.

Correlation with the Clinical Outcomes of the Patients

Figure 2:
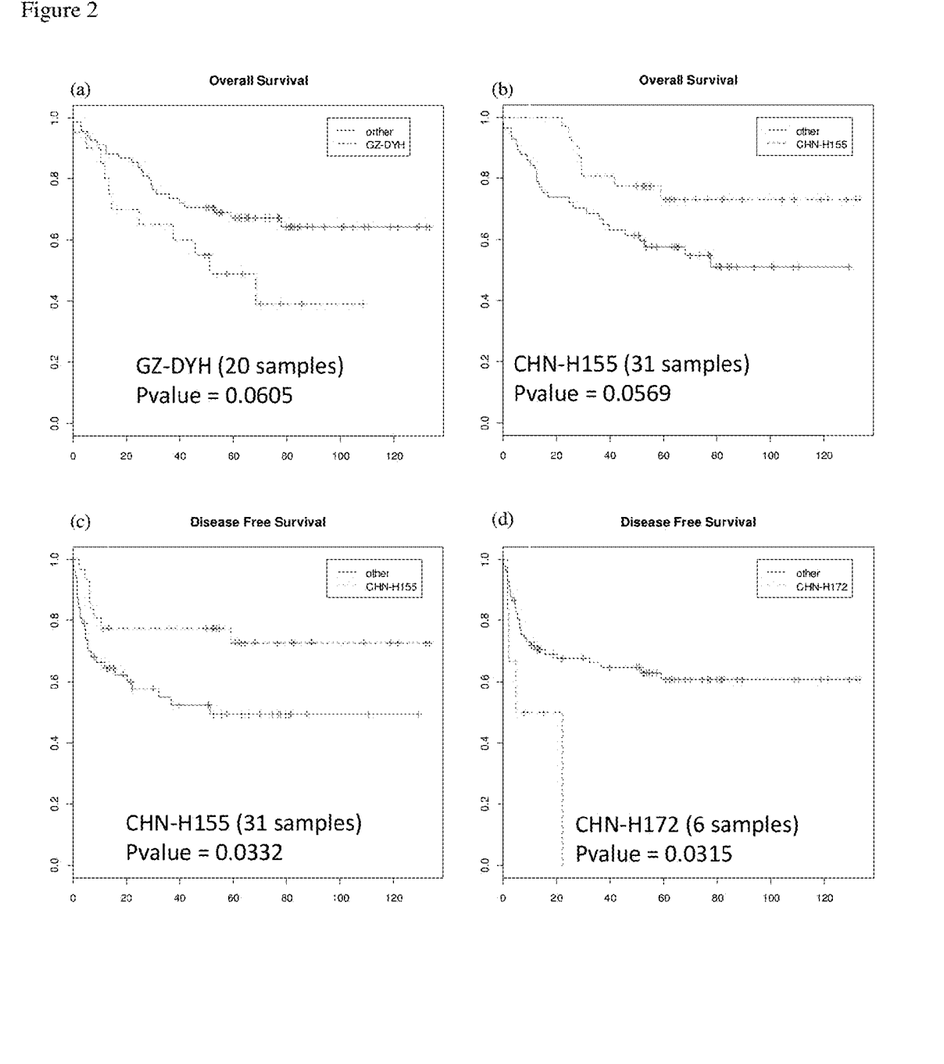
FIG. 2 are the survival curves for GZ-DYH, CHN-H155, and CHN-172.

Next, the relationship between HBV strains and clinical outcome was examined. FIG. 2 depicts the survival curves of patients with GZ-DYH, CHN-H155, and CHN-172 strains. Patients carrying CHN-H155 had better survival than patients with GZ-DYH and CHN-H172 strains.

Recurrent and venous infiltration were more likely to appear in patients carrying CHN-H172 (p-values=0.01303 and 0.03323 respectively). On the other hand, recurrent and venous infiltration were less likely to appear in patients carrying CHN-155 (p-values=0.006756 and 0.07714 respectively). The chance of a patient having both recurrent and venous infiltration given that the patient carry a particular type of HBV strain was computed. Patients who carried CHN-H172, GZ-DYH and HBV-B2 had a higher chance to have both recurrent and venous infiltration (p-values=0.0, 0.02384, and 0.1837) whilst patients who carried CHN-155 were likely to not have recurrence and venous infiltration (p-value=0.178).

TABLE 4

Locations of HBV integrations for HCC patients with different HBV strains.

| HBV strain | Exon | | | Intron | | | Promoter | | |
|---|---|---|---|---|---|---|---|---|---|
| | Number | Fraction | p-value | Number | Fraction | p-value | Number | Fraction | p-value |
| CHN-H155 | 7 | 0.4375 | 0.371537 | 54 | 0.432 | 0.086925 | 18 | 0.580645 | 0.013351 |
| GZ-DYH | 4 | 0.25 | 0.551154 | 33 | 0.264 | 0.27858 | 8 | 0.258065 | 0.465166 |
| HBV-B2 | 3 | 0.1875 | 0.85589 | 22 | 0.176 | 0.996082 | 3 | 0.096774 | 0.996118 |
| CHN-H172 | 2 | 0.125 | 0.318447 | 14 | 0.112 | 0.063022 | 2 | 0.064516 | 0.659761 |

Other clinical parameters were also studied and some significant associations are as follows. Patients who carried GZ-DYH had a higher chance of having cirrhosis (p-value=0.01959, Table 1). Patients who carried HBV-B2 had bigger tumors (p-value=0.05546) and their Edmondson grade were likely to be poorly differentiated (p-value=0.02964, Table 1).

Mutation C2288A of CHN-H155 and HBV-TERT Integration

Out of thirty-one patients who carried CHN-H155, 13 of them had HBV-TERT integration. It was investigated whether HBV-TERT integration is associated with mutation in CHN-H155, specifically a C2288A mutation that was identified. This mutation affects the precore/core protein on CHN-H155 and mutates the codon "CCC" (encoding the non-polar proline, P) to "ACC" (encoding the polar threonine, T). It was observed that this mutation significantly reduced the chance of HBV-TERT integration (p-value=0.02, odds ratio=6.2). Out of 31 samples, 15 of them had the mutation C2288A. Only 3 of these 15 samples had HBV-TERT integration. These 15 samples did not have significant correlation with clinical outcome.

For the remaining 16 samples with no C2288A mutation, 10 of them had the HBV-TERT integration, which were significantly associated with clinical outcome. In these patient samples, venous infiltration was absent in these samples (p-value=0.0507), no recurrence was observed (p-value=0.00412), and the overall and disease free survival were good (p-value=0.00518 and 0.00456 respectively).

CHN-H155. Out of these thirty-one patients, 13 of them have HBV-TERT integration. As there are only 18 samples with HBV-TERT integrations, patients carrying CHN-H155 have higher risk to have HBV-TERT integration (p-value is 0.000404 by Fisher exact test). The expression profiles of these samples are mostly S3 (10 out of 13). Patients with expression profile S3 have better survival. This explains why CHN-H155 carriers have better survival. (Note: Out of 18 patients with HBV-TERT integration, 3, 2 and 13 of them are in S1, S2 and S3 respectively. Hence, patients with HBT-TERT are likely to have expression profile S3.)

Furthermore, the mutation C2288A on CHN-H155 was identified to determine the risk of having a HBV-TERT integration. Out of thirty-one patients, 16 of them did not have this mutation and they tend to have HBV-TERT integration (10 cases, p-value=0.02).

This study suggested that it is important for HBV carriers to know the exact HBV strains carried by them. Depending on the HBV strain carried by the HBV carrier, the patient may be assigned to a different treatment and/or prevention scheme (see Table 5).

When the HBV carriers developed HCC, the HBV strains can help to suggest potential treatment (see Table 5).

Lastly, this study was conducted using patient samples from Hong Kong whose HBV strains are mainly of genotype C. It is important to study samples from other Asian countries.

TABLE 5

Potential treatment and prevention schemes for HCC patients carrying different HBV strains.

| HBV strain | Treatment scheme | Prevention scheme |
|---|---|---|
| CHN-H155 | These patients have less chance of recurrent and Venous Infiltration if C2288. Those patients need to take TERT related drug. They also can consider undergoing liver resection. | Need to monitor if HBV is integrated into TERT genes. Once it is integrated, they need to take TERT related drug. |
| GZ-DYH | When HBV-MLL4 appears in the tumor, the patients may need to take p53 related drug since MLL4 is a p53 co-activator | Need to monitor if HBV is integrated into MLL4 genes |
| HBV-B2 | When HBV-MLL4 appears in the tumor or p53 is mutated, the patients may need to take p53 related drug since MLL4 is a p53 co-activator | Need to monitor if HBV is integrated into MLL4 genes and if p53 is mutated |
| CHN-H172 | These patients have high chance of recurrent and Venous Infiltration. Even if they remove the tumor tissue, they need to monitor closely. | |

HBV strains were detected by nucleic acid sequencing or suitable PCR methods.

To increase the confidence during the identification of the HBV strains, primers as described by Naito et al.[14] may be used to determine if the sample is of genotype B or C.

Discussion

HCC patients carrying different HBV strains have different genomic profiles, which in turn result in different clinical outcomes. One observation is that the clinical outcome of HBV is not purely depending on genotypes. For instance, although both CHN-H155 and GZ-DYH are of subgenotype Cs, CHN-H155 and GZ-DYH have different clinical outcomes. CHN-H155 carriers have better survival and fewer recurrences while GZ-DYH carriers trend to have worst survival and more recurrences.

In particular, this disclosure understands more the mechanism of CHN-H155. Out of 88 samples, 31 patients carry

REFERENCES

1. Arguedas M R et al. "Screening for hepatocellular carcinoma in patients with hepatitis C cirrhosis: a cost-utility analysis", Am J Gastroenterol 2003; 98:679-90
2. Raimondi S et al. "Hepatitis C virus genotype 1 b as a risk factor for hepatocellular carcinoma development: a meta-analysis", Journal of Hepatology 2009; 50:1142-54
3. Roffi L et al. "Outcome of liver disease in a large cohort of histologically proven chronic hepatitis C: influence of HCV genotype", Eur J Gastroenterol Hepatol 2001; 13:501-6
4. Mahtab M A et al. "Hepatitis B virus genotypes: an overview", Hepatobiliary Pancreat Dis Int 2008; 7:457-64
5. Chan, H L Y, et al. "Genotype C hepatitis B virus infection is associated with an increased risk of hepatocellular carcinoma", Gut (2004) 53:1494-1498.

6. Kao, J H, et al. "Basal core promoter mutations of hepatitis B virus increase the risk of hepatocellular carcinoma in hepatitis B carrier", Gastroenterology (2003) 124:327-334.
7. Yu, M W, et al. "Hepatitis B virus genotype and DNA level and hepatocellular carcinoma: a prospective study in men", J. Natl. Cancer Inst. (2005) 97:265-272.
8. Midorikawa et al. "Microarray-based analysis for hepatocellular carcinoma: from gene expression profiling to new challenges", World J Gastroenterol 2007, 13(10):1487-1492
9. Sung et al. "Genotype-specific genomic markers associated with primary hepatomas, based on complete genomic sequencing of hepatitis B virus", J Virol 2008; 82:3604-11
10. Hao K et al. "Predicting prognosis in hepatocellular carcinoma after curative surgery with common clinico-pathologic parameters", BMC Cancer 2009; 9:389
11. Xu X et al. "The genomic sequence of the Chinese hamster ovary (CHO)-K1 cell line", Nat Biotechnol 2011; 29:735-41
12. Kan Z Y et al. "Whole-genome sequencing identifies recurrent mutations in hepatocellular carcinoma", Genome Res 2013; 23:1422-1433.
13. Hoshida Y et al. "Integrative transcriptome analysis reveals common molecular subclasses of human hepatocellular carcinoma", Cancer Res 2009; 69:7385-92
14. Naito H et al. "Rapid and specific genotyping system for hepatitis B virus corresponding to six major genotypes by PCR using type-specific primers", J Clin Microbiol 2001; 39(1):362-4.

The invention claimed is:

1. A method comprising the steps of:
   a) detecting the presence of a Hepatitis B virus (HBV) in a sample obtained from a patient having hepatocellular carcinoma (HCC);
   b) identifying the genotype and strain of said HBV in said sample, wherein the genotype and strain is selected from the group consisting of CHN-H155 (genotype C), GZ-DYH(genotype C), CHN-H172 (genotype C) and HBV-B2 (genotype B); and
   c) administering a treatment and/or prevention scheme for HCC to the patient based upon the genotype and strain of HBV identified in b)
   wherein when CHN-H155 is detected, the patient is monitored for HBV integration into a TERT gene and treated with a TERT related drug and/or a liver resection if integration has occurred;
   wherein when GZ-DYH is detected, the patient is monitored for HBV integration into a MLL4 gene and treated with a p53 related drug if integration has occurred;
   wherein when HBV-B2 is detected, the patient is monitored for HBV integration into a MLL4 gene and mutation in a p53 gene and treated with a p53 related drug if integration and mutation has occurred;
   wherein when CHN-H172 is detected, the patient is treated with surgery to remove the tumor and monitored for tumor recurrence.

2. A method comprising the steps of:
   a) detecting the presence of a Hepatitis B virus (HBV) in a sample obtained from a patient having hepatocellular carcinoma (HCC), wherein the sample comprises a nucleic acid, wherein the nucleic acid sample is amplified by polymerase chain reaction (PCR) into one or more amplicons, wherein the one or more amplicons are subjected to sequencing, or ii) subjected to whole genome sequencing;
   b) identifying the genotype and strain of said HBV in said sample by comparing the sequence of the one or more amplicons obtained in ai) or with the genome sequence obtained in aii) with sequences of known HBV genotypes and strains,
   wherein the genotype and strain is selected from the group consisting of CHN-H155 (genotype C), GZ-DYH(genotype C), CHN-H172 (genotype C) and HBV-B2 (genotype B); and
   c) administering a treatment and/or prevention scheme for HCC to the patient based upon the genotype and strain of HBV identified in b)
   wherein when CHN-H155 is detected, the patient is monitored for HV integration into a TERT gene and treated with a TERT related drug and/or a liver resection if integration has occurred;
   wherein when GZ-DYB is detected, the patient is monitored for HBV integration into a MLL4 gene and treated with a p53 related drug if integration has occurred;
   wherein when HBV-B2 is detected, the patient is monitored for HBV integration into a MLL4 gene and mutation in a p53 gene and treated with a p53 related drug if integration and mutation has occurred;
   wherein when CHN-H172 is detected, the patient is treated with surgery to remove the tumour and monitored for tumour recurrence.

3. A method comprising the steps of:
   a) detecting the presence of a Hepatitis B virus (HBV) in a sample obtained from a patient having hepatocellular carcinoma (HCC), wherein the sample comprises a nucleic acid, wherein the nucleic acid sample is amplified by polymerase chain reaction (PCR) into one or more amplicons using oligonucleotide groups SEQ ID NO: 13 and SEQ ID NO: 15; SEQ ID NO: 16 and SEQ ID NO: 18; SEQ ID NO: 19 and SEQ ID NO: 21; SEQ ID NO: 22 and SEQ ID NO: 24; SEQ ID NO:
   25 and SEQ ID NO: 27; or SEQ ID NO: 28 and SEQ ID NO: 30; wherein the one or more amplicons are subjected to sequencing;
   b) identifying the genotype and strain of said HBV in said sample by comparing the sequence of the one or more amplicons obtained in a) with sequences of known HBV genotypes and strains,
   wherein the genotype and strain is selected from the group consisting of CHN-H155 (genotype C), GZ-DYH (genotype C), CHN-H172 (genotype C) and HBV-B2 (genotype B); and
   c) administering a treatment and/or prevention scheme for HCC to the patient based upon the genotype and strain of HBV identified in b), wherein when CHN-H155 is detected, the patient is monitored for HBV integration into a TERT gene and treated with a TERT related drug and/or a liver resection if integration has occurred;

wherein when GZ-DYH is detected, the patient is monitored for HBV integration into a MLL4 gene and treated with a p53 related drug if integration has occurred;

wherein when HBV-B2 is detected, the patient is monitored for HBV integration into a MLL4 gene and mutation in a p53 gene and treated with a p53 related drug if integration and mutation has occurred;

wherein when CHN-H172 is detected, the patient is treated with surgery to remove the tumour and monitored for tumour recurrence.

* * * * *

SEQUENCE LISTING

```
<160> NUMBER OF SEQ ID NOS: 33

<210> SEQ ID NO 1
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 1
ctacagcatg ggaggttggt                                                    20

<210> SEQ ID NO 2
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 2
ctccacccca cggcagtctt                                                    20

<210> SEQ ID NO 3
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 3
gctgctggca ctgttgtcaa                                                    20

<210> SEQ ID NO 4
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 4 tccctttta ccgctgttac c                                                   21

<210> SEQ ID NO 5
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 5
```
tactaaaact aaacgttggg                                              20

<210> SEQ ID NO 6
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 6
ccccacaatt cgttgacata                                              20

<210> SEQ ID NO 7
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 7
ttgggggagg agactaggtt                                              20

<210> SEQ ID NO 8
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 8
gttcatgtct cactgttcaa                                              20

<210> SEQ ID NO 9
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 9
tcaatgtcca tgccccaaag                                              20

<210> SEQ ID NO 10
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 10
gctttcactt tctcgccaac                                              20

<210> SEQ ID NO 11
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 11
aaaactcatc ggaaccgaca                                              20

<210> SEQ ID NO 12
<211> LENGTH: 20
<212> TYPE: DNA

```
<213> ORGANISM: Artificial Sequence
<220> FEATURE:
<223> OTHER INFORMATION: A synthetic oligonucleotide

<400> SEQUENCE: 12
ctagcagcca tggaaaggag                                               20

<210> SEQ ID NO 13
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 13
ctgggaggct gtaggcataa                                               20

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 14 cttttttcact cctgcctaat                                              20

<210> SEQ ID NO 15
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 15
atacagagca gaggcggtgt                                               20

<210> SEQ ID NO 16
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 16
tattgggggc caagtctgta                                               20

<210> SEQ ID NO 17
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 17
tcccttaacc ttatgggata                                               20

<210> SEQ ID NO 18
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 18
gtgtaaaagg ggcagcaaag                                               20
```

```
<210> SEQ ID NO 19
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 19
ggcaaactcc ctcttttcct                                                20

<210> SEQ ID NO 20
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 20
cctgaacaca tagttaatca                                                20

<210> SEQ ID NO 21
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 21
aggcgctgcg agtagtttct                                                20

<210> SEQ ID NO 22
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 22
ttgggggcca agtctgta                                                  18

<210> SEQ ID NO 23
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 23
atattgtaag aaaaatcaaa                                                20

<210> SEQ ID NO 24
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 24
tatccacatt gcgtgaaagg                                                20

<210> SEQ ID NO 25
<211> LENGTH: 20
<212> TYPE: DNA
<213> ORGANISM: Artificial Sequence
<220> FEATURE:
```

```
<223> OTHER INFORMATION: A synthetic oligonucleotide

<400> SEQUENCE: 25
catgaacctt taccccgttg                                              20

<210> SEQ ID NO 26
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 26
caagtgtttc gtgacgcaac                                              20

<210> SEQ ID NO 27
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 27
gacgggacgt aaacaaagga                                              20

<210> SEQ ID NO 28
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 28
actgttcttg agtatttggt g                                            21

<210> SEQ ID NO 29
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 29
tcgcactcct cccgcttaca g                                            21

<210> SEQ ID NO 30
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 30
tgacatctat tgataatatc ctctttc                                      27

<210> SEQ ID NO 31
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 31
actgttcttg agtatttggt g                                            21
```

```
<210> SEQ ID NO 32
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 32
tcgcactcct accgcttaca g                                             21

<210> SEQ ID NO 33
<211> LENGTH: 27
<212> TYPE: DNA
<213> ORGANISM: Artificial Sequence
<220> FEATURE:
<223> OTHER INFORMATION: A synthetic oligonucleotide

<400> SEQUENCE: 33
tgacatctat tgataatatc ctctttc                                       27
```